United States Patent
Mackenzie et al.

(10) Patent No.: US 11,806,501 B2
(45) Date of Patent: *Nov. 7, 2023

(54) EMERGENCY MEDICAL INTERVENTION DEVICE

(71) Applicant: Corvictus, LLC, Newark, DE (US)

(72) Inventors: Samuel Mackenzie, Columbus, OH (US); John Mackenzie, Newark, DE (US)

(73) Assignee: CORVICTUS, LLC, Newark, DE (US)

( * ) Notice: Subject to any disclaimer, the term of this patent is extended or adjusted under 35 U.S.C. 154(b) by 264 days.

This patent is subject to a terminal disclaimer.

(21) Appl. No.: 17/151,260

(22) Filed: Jan. 18, 2021

(65) Prior Publication Data

US 2021/0128821 A1    May 6, 2021

Related U.S. Application Data

(63) Continuation of application No. 16/151,679, filed on Oct. 4, 2018, now Pat. No. 10,926,024.

(51) Int. Cl.
*A61M 5/14*   (2006.01)
*A61M 5/162*   (2006.01)
(Continued)

(52) U.S. Cl.
CPC ...... *A61M 5/1408* (2013.01); *A61M 5/14224* (2013.01); *A61M 5/14228* (2013.01);
(Continued)

(58) Field of Classification Search
CPC ........ A61M 5/00; A61M 5/14; A61M 5/1407; A61M 5/142; A61M 2005/1401;
(Continued)

(56) References Cited

U.S. PATENT DOCUMENTS

| 4,850,972 A | 7/1989 | Schulman et al. |
| 5,207,642 A | 5/1993 | Orkin et al. |

(Continued)

OTHER PUBLICATIONS

Todd B. Brown et al., "Relationship Between Knowledge of Cardiopulmonary Resuscitation Guidelines and Performance", Department of Emergency Medicine, University of Alabama, Birmingham, AL, USA, Resuscitation Elsevier, (2006) vol. 69, pp. 253-261.

(Continued)

*Primary Examiner* — Jason E Flick

(57) ABSTRACT

A therapeutic device for treating an acute medical condition of a patient such as cardiac arrest is provided. The device includes one or more sensors that monitor parameters such as heart rhythm that relate to the patient's medical condition. The device also includes a plurality of medication reservoirs, each reservoir including a conduit, wherein each reservoir holds a predetermined medication that may be used to treat the condition. A manifold is connected with the reservoirs via their respective conduits. A delivery line is connected with the manifold to deliver fluids from the manifold to the patient intravenously. One or more medication pumps are in fluid connection with respective ones of the reservoirs. A processor is connected with the sensors. The processor includes a memory that stores processing instructions to interpret the parameters and to determine a recommended medication to deliver to the patient based on the parameters, the recommended medication being one of the predetermined medications. The processor is operatively connected with the medication pumps. When a recommended medication is determined, the processor actuates the medication pump connected with the reservoir including the recommended medication to deliver the medication to the patient via the manifold and the delivery line.

20 Claims, 7 Drawing Sheets

(51) Int. Cl.
  *A61N 1/39* (2006.01)
  *A61N 1/362* (2006.01)
  *A61M 5/142* (2006.01)
  *A61M 5/145* (2006.01)
  *A61N 1/365* (2006.01)
  *A61M 5/168* (2006.01)

(52) U.S. Cl.
  CPC ........ *A61M 5/14546* (2013.01); *A61M 5/162* (2013.01); *A61M 5/16813* (2013.01); *A61N 1/365* (2013.01); *A61N 1/3625* (2013.01); *A61N 1/3987* (2013.01); *A61M 2005/1403* (2013.01); *A61M 2205/3592* (2013.01); *A61M 2205/50* (2013.01); *A61M 2205/502* (2013.01); *A61M 2205/505* (2013.01); *A61M 2205/52* (2013.01); *A61M 2205/581* (2013.01); *A61M 2230/06* (2013.01); *A61M 2230/20* (2013.01); *A61M 2230/30* (2013.01); *A61M 2230/43* (2013.01)

(58) Field of Classification Search
  CPC .......... A61M 2230/04; A61M 2230/00; A61M 2230/40; A61M 2005/1403; A61M 2205/3592; A61M 2205/50; A61M 2205/502; A61M 2205/505; A61M 2205/52; A61M 2205/581; A61M 2230/06; A61M 2230/20; A61M 2230/30; A61M 2230/43; A61M 5/1408; A61M 5/14224; A61M 5/14228; A61M 5/14546; A61M 5/162; A61M 5/16813; A61N 1/3625; A61N 1/365; A61N 1/3987; A61N 1/3904
  See application file for complete search history.

(56) References Cited

U.S. PATENT DOCUMENTS

| | | | |
|---|---|---|---|
| 5,298,021 | A | 3/1994 | Sherer |
| 7,316,231 | B2 | 1/2008 | Hickle |
| 7,575,567 | B2 | 8/2009 | Simpkins |
| 7,608,060 | B2 | 10/2009 | Gillespie, Jr. et al. |
| 7,815,605 | B2 | 10/2010 | Souter |
| 7,917,208 | B2 | 3/2011 | Yomtov et al. |
| 7,963,945 | B2 | 6/2011 | Miller et al. |
| 8,812,101 | B2 | 8/2014 | Miller et al. |
| 9,398,894 | B2 | 7/2016 | Patrick et al. |
| 10,668,247 | B2 | 6/2020 | Anand et al. |
| 10,675,438 | B2 | 6/2020 | Anand et al. |
| 10,682,067 | B2 | 6/2020 | Tan et al. |
| 10,828,424 | B2 | 11/2020 | Anand et al. |
| 10,926,024 | B2 | 2/2021 | Mackenzie et al. |
| 2010/0022987 | A1 | 1/2010 | Bochenko et al. |
| 2010/0198280 | A1 | 8/2010 | Corndorf et al. |
| 2013/0296823 | A1* | 11/2013 | Melker ............. A61M 5/16854 604/503 |
| 2020/0155401 | A1 | 5/2020 | Wang et al. |
| 2020/0297966 | A1 | 9/2020 | Anand et al. |
| 2021/0052820 | A1 | 2/2021 | Anand et al. |
| 2021/0085859 | A1 | 3/2021 | Oshinski et al. |

OTHER PUBLICATIONS

Kathy Dittrich, "ACLS update: A new role for medications," Critical Care, www.nursing2007.com, December, Nursing2007, pp. 56cc1-56cc3.

Alexander H. Flannery et al., "Medication Errors in Cardiopulmonary Arrest and Code-Related Situations", AJCC American Journal of Critical Care, Jan. 2016, vol. 25, No. 1, pp. 12-20.

ISMP Institute for Safe Medication Practices, "Two Unsafe Practices: Administration of a Product with a Precipitate and Reuse of a Saline Flush Syringe," Featured Articles, online, <https://www.ismp.org/resources/two-unsafe-practices-administration-product-precipitate-and-reuse-saline-flush-syringe> Apr. 6, 2017, 6 pages.

Phil Jevon, "The Administration of Drugs During Resuscitation," Clinical Practical Procedures, Nursing Times, vol. 103, No. 11, www.nursingtimes.net, Mar. 13, 2007, pp. 26-27.

Luer-Jet™ "Needleless Emergency Syringes," International Medication Systems, Ltd., An Amphastar Pharmaceuticals Company, www.ims-limited.com, Rx Only Apr. 2019, 2 pages.

Tara Mccurdie et al., "The Use of Multiple Methods to Explore the Impact of Interruptions on Intravenous (IV) Push Delivery," Proceedings of the Human Factors and Ergonomics Society 58th Annual Meeting—Oct. 2014, pp. 738-742.

Dariush Mozaffarian et al., "Executive Summary: Heart Disease and Stroke Statistics—2015 Update A Report From the American Heart Association", UC San Francisco Previously Published Works, Jan. 27, 2015, pp. 434-441.

Chika Nishiyama et al., "Long-term Retention of Cardiopulmonary Resuscitation Skills After Shortened Chest Compression-only Training and Conventional Training: A Randomized Controlled Trial", Academic Emergency Medicine, Official Journal of the Society for Academic Emergency Medicine, 2013, pp. 47-54.

Office Action for U.S. Appl. No. 16/151,679, dated Oct. 27, 2023.

* cited by examiner

EMERGENCY MEDICAL INTERVENTION DEVICE

CROSS REFERENCE TO RELATED APPLICATIONS

This application is a continuation of co-pending application Ser. No. 16/151,679, filed Oct. 4, 2018, which is incorporated herein in its entirety by reference.

BACKGROUND

Field

This disclosure relates to systems, apparatuses, applications, methodologies and other tools to administer medications and other treatments to patients experiencing an acute medical condition, such as cardiac arrest. In particular, this disclosure relates to a system for monitoring the condition of a patient experiencing an acute medical condition, determining a protocol of medications and/or electrical stimulation to treat the condition, delivering the treatment, providing feedback to medical professionals attending to the patient regarding the patient's condition, and creating a record of medical treatments.

Description of the Related Art

Heart disease is the leading cause of death worldwide with 17.3 million deaths each year. That number is expected to rise further by 2030 to 23.6 million. Conditions such as hypertension, hyperlipidemia, electrolyte imbalances, and trauma may lead to cardiac arrest where the patient's heart cannot provide adequate blood supply to vital organs, leading to severe injury or death. Cardiac arrest also compromises blood flow to the heart itself, leading to ischemia. Providing proper medical intervention soon after the onset of cardiac arrest is vital. In the United States, only about 10% of people who sustain a cardiac arrest survive it. The survival rate triples when an arrest is witnessed by a bystander who can provide immediate assistance by administering cardiopulmonary resuscitation CPR and/or by summoning aid.

A "code" is a medical term used to describe a situation where a patient requires resuscitative efforts by a team of medical professionals, usually because the patient is experiencing cardiopulmonary arrest. Cardiopulmonary arrest may be due to various underlying causes resulting in an abnormal heartbeat or the absence of a heartbeat. Generally, treatments provided during a code focus on resuscitative efforts to restore a normal or near normal heartbeat to maintain blood flow throughout the body. Because vital organs and the central nervous system can be injured by interruption of blood flow for even short amounts of time, medical treatment during a code needs to be performed quickly. Often decisions to administer treatment during a code are complex and depend on the patient's medical condition, which may change from moment to moment.

Common interventions performed during a code include chest compressions (to compensate for a patient's heart not beating normally on its own), rescue breathing (to increase the level of oxygen in circulating blood), electrical shocks (to stimulate a patient's heart to beat normally), and various medications (to stimulate the heart or change the rhythm in which the heart is beating). Non-medical rescuers may learn skills focused on the first two of these interventions as part of Basic Life Support (BLS). Additionally, people trained in BLS may learn how to use an Automated External Defibrillator (AED), a device that interprets a patient's heart rhythm and potentially delivers an electrical shock based on that interpretation. BLS and use of an AED are based on established protocols. For example, BLS includes determining the patient's condition and administering chest compressions, rescue breathing, and/or electrical stimulation with an AED.

Medical professionals (e.g., emergency responders, nurses, pharmacists, physicians, nurse practitioners, physician assistants, etc.) may learn a more advanced form of intervention that, like BLS, is also largely protocol-based. For adult patients, this set of protocols is known as Advanced Cardiac Life Support (ACLS). For children, this is known as Pediatric Advanced Life Support (PALS). ACLS and PALS focus on additional medication delivery and rescuer-selected electrical intervention based on a rescuer's interpretation of various cardiac rhythms. PALS is similar to ACLS but it utilizes weight-based medication dosages.

In-hospital cardiac arrests and out-of-hospital arrests are treated somewhat differently based on the fact that more highly-trained medical professionals and other resources are readily available in the hospital. Medications are more commonly administered in the hospital setting.

Code situations are often chaotic, with life-or-death decisions being made by a code leader and communicated to other professionals verbally and under time pressure. These circumstances can lead to errors in treatment. For example, the code leader's instructions regarding the medication, dosage, or route of administration may be misunderstood by team members, e.g., instructions to administer 1 mg of 1:1,000 concentration epinephrine instead of the appropriate 1:10,000 concentration. Likewise, delivery of treatment such as chest compressions and electrical shock may be incorrect because of inexperience of team members or miscommunication. In addition, there may be errors in how medications are prepared or labeled, or which medication is actually administered because packaging or labeling of different medications look similar.

The time stress of a code situation also makes it difficult to create a record of what treatments were administered, at what time, and in the context of the patient's condition. In the case of cardiac arrest, the patient's condition may change rapidly. Decisions by the code leader and other code team members are made in response to the patient's condition and there may not be time to record what was done. Poor recordkeeping during the code may make it difficult for team members and other professionals to learn how to improve or to assess whether proper treatment was given.

Accordingly, there is a need for a system to monitor patients experiencing acute, life threatening conditions, such as cardiac arrest, to reliably administer treatments including medications and electrical shocks to restore healthier cardiac rhythm, and to create a record of the treatments administered to the patient.

SUMMARY

The present disclosure relates to apparatuses and methods to address these difficulties.

A device according to an embodiment of the disclosure provides a semi-automated medication delivery system to reduce medication errors for in-hospital and out-of-hospital cardiac arrests. According this embodiment a therapeutic device comprises one or more sensors, the sensors adapted to monitor parameters of an organism, the parameters relating to an acute medical condition; a plurality of medication reservoirs, each reservoir including a conduit, wherein each reservoir holds a predetermined medication; a manifold in fluid connection with the reservoirs via their respective conduits; a delivery line connected with the manifold, the delivery line adapted to deliver fluids from the manifold into the organism; one or more medication pumps, each medication pump in fluid connection with a respective one of the reservoirs; and a processor connected with the sensors, the processor including a memory storing processing instructions to interpret the parameters and to determine a recommended medication to deliver to the organism based on the parameters, the recommended medication being one of the predetermined medications, wherein the processor is operatively connected with the medication pumps and wherein, when a recommended medication is determined, the processor actuates the medication pump connected with the reservoir including the recommended medication to deliver the medication to the organism via the manifold and the delivery line.

According to an aspect of the disclosure the conduits are connected with the manifold by respective one-way valves. According to a further aspect of the disclosure, the device further comprises a flush reservoir holding a flush fluid in fluid connection with the manifold; and a flush pump in fluid connection with the flush reservoir, wherein the flush pump is operatively connected with the processor and wherein when the processor delivers the recommended medication, the processor actuates the flush pump to deliver a volume of the flush fluid to the manifold to flush the recommended medication from the manifold. According to another aspect of the disclosure the medication reservoirs include a mechanism for withdrawing or delivering medications not initially housed within the device such as via a perforatable membrane that can be penetrated by a hypodermic needle or similar penetrating instrument. According to another aspect of the disclosure the device further comprises a waste diverting valve in fluid connection with the manifold and the delivery line; a diverting valve actuator in mechanical connection with the diverting valve and operatively connected with the processor to actuate the diverter valve; and a waste reservoir in fluid connection with the waste diverting valve, wherein when the waste diverting valve is actuated by the processor, fluid flowing from the manifold is diverted away from the delivery line and into the waste reservoir. According to another aspect of the disclosure the medication pumps are one or more of peristaltic pumps, syringe pumps, or elastomeric pumps. According to another aspect of the disclosure, the device further comprises a liquid handling assembly comprising the medication reservoirs, the conduits, the manifold, and the waste diverting valve; and a chassis comprising the sensors, the processor, a plurality of pump motors, and the diverting valve actuator, wherein the liquid handling assembly is shaped to be removably fitted into the chassis. According to another aspect of the disclosure the sensor includes a 12-lead electrocardiogram apparatus. According to another aspect of the disclosure the acute condition is a cardiac arrhythmia. According to another aspect of the disclosure the organism is a human. According to another aspect of the disclosure the device further comprises a plurality of releasable connections between respective ones of the medication reservoirs and the conduits, wherein one or more of the medication reservoirs can be removed and replaced.

According to another embodiment of the disclosure a method of treating an organism comprises the steps of: providing one or more sensors, the sensors adapted to monitor parameters of an organism, the parameters relating to an acute medical condition; providing a plurality of medication reservoirs, each reservoir including a conduit, wherein each reservoir holds a predetermined medication; providing a manifold in fluid connection with the reservoirs via their respective conduits; providing a delivery line connected with the manifold, the delivery line adapted to deliver fluids from the manifold into the organism; providing one or more medication pumps, each medication pump in fluid connection with a respective one of the reservoirs; providing a processor connected with the sensors, the processor including a memory storing processing instructions to interpret the parameters and to determine a recommended medication to deliver to the organism based on the parameters, the recommended medication being one of the predetermined medications, wherein the processor is operatively connected with the medication pumps; providing a flush reservoir holding a flush fluid in fluid connection with the manifold; providing a flush pump in fluid connection with the flush reservoir, wherein the flush pump is operatively connected with the processor; connecting the sensors to the organism; connecting the delivery line to the organism; determining that a condition of the organism is to be treated with a recommended medication; actuating, by the processor, the medication pump connected with the reservoir including the recommended medication to deliver the medication into the manifold; actuating, by the processor, the flush pump wherein flush fluid is delivered to the manifold and wherein the medication, mixed with the flush fluid is delivered to the organism via the manifold and the delivery line.

According to another aspect of the disclosure the method further comprises providing a waste diverting valve in fluid connection with the manifold and the delivery line; providing a diverting valve actuator in mechanical connection with the diverting valve and operatively connected with the processor to actuate the diverter valve; providing a waste reservoir in fluid connection with the waste diverting valve, wherein when the waste diverting valve is actuated by the processor, fluid flowing from the manifold is diverted away from the delivery line and into the waste reservoir; actuating, by the processor, the diverting valve to divert fluid from the manifold into the waste reservoir; actuating, by the processor, the flush pump to deliver flush fluid into the manifold to push a volume of fluid into the waste reservoir, the volume being sufficient to clear medication from the fluid in the manifold.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

During a cardiac arrest, protocols such as ACLS and PALS indicate how and when interventions including electrical shocks and/or medications should be administered based on the patient's heart rhythm. These rhythms broadly include: 1) Pulseless Electrical Activity (PEA) or asystole; 2) Ventricular Fibrillation or Pulseless Ventricular Tachycardia (VF/VT); 3) Bradycardia; and 4) Tachycardia. Identification of the patient's heart rhythm can be determined through computer analysis of sensor data such as from an ECG.

The present disclosure is directed to a system that receives data about the patient's heart rhythm and other information, such as the patient's age, weight, medical history, blood pressure, and the like, applies an algorithm to determine a protocol for treatment, and applies the treatment, including administering medications and electrical stimulation. The system is equipped with drug delivery apparatus to administer appropriate medication and may be connected with apparatus to administer electrical energy to shock the heart into a normal rhythm or may be connected with implanted or transdermal pacing electrodes to capture and modulate a patient's heart rhythm. According to a further embodiment, the system interfaces with a patient's previously implanted cardioverter and receives heart rhythm information from the cardioverter and/or controls the administration of electrical stimulation by the cardioverter as part of a treatment protocol.

According to one embodiment, such a system is located in a hospital setting. The system might be stored on a so-called "crash cart" or in an easily accessible location in an emergency room or intensive care unit so that it can be quickly deployed in a code situation. In such a setting, the system may provide information to code team members regarding treatment, such as whether chest compressions are being applied properly or whether electrical stimulation should be applied. The system may also administer medications according to a protocol, e.g. ACLS or PALS, either autonomously, or else prompt code team members for authorization to administer medications. According to a further embodiment, medical personnel can optionally override the protocol to deliver medications and/or electrical stimulation in appropriate situations.

According to another embodiment, the system could be located outside the hospital, for example, in an ambulance or other emergency response vehicle to administer treatment to a patient in the field, or as the patient is en route to the hospital after sustaining a cardiopulmonary arrest. Such a system may be integrated with systems at the hospital operated by code team members to provide remote assistance for rescuers responding to cardiopulmonary arrest in the field through various forms of electronic communication.

Figure 1:
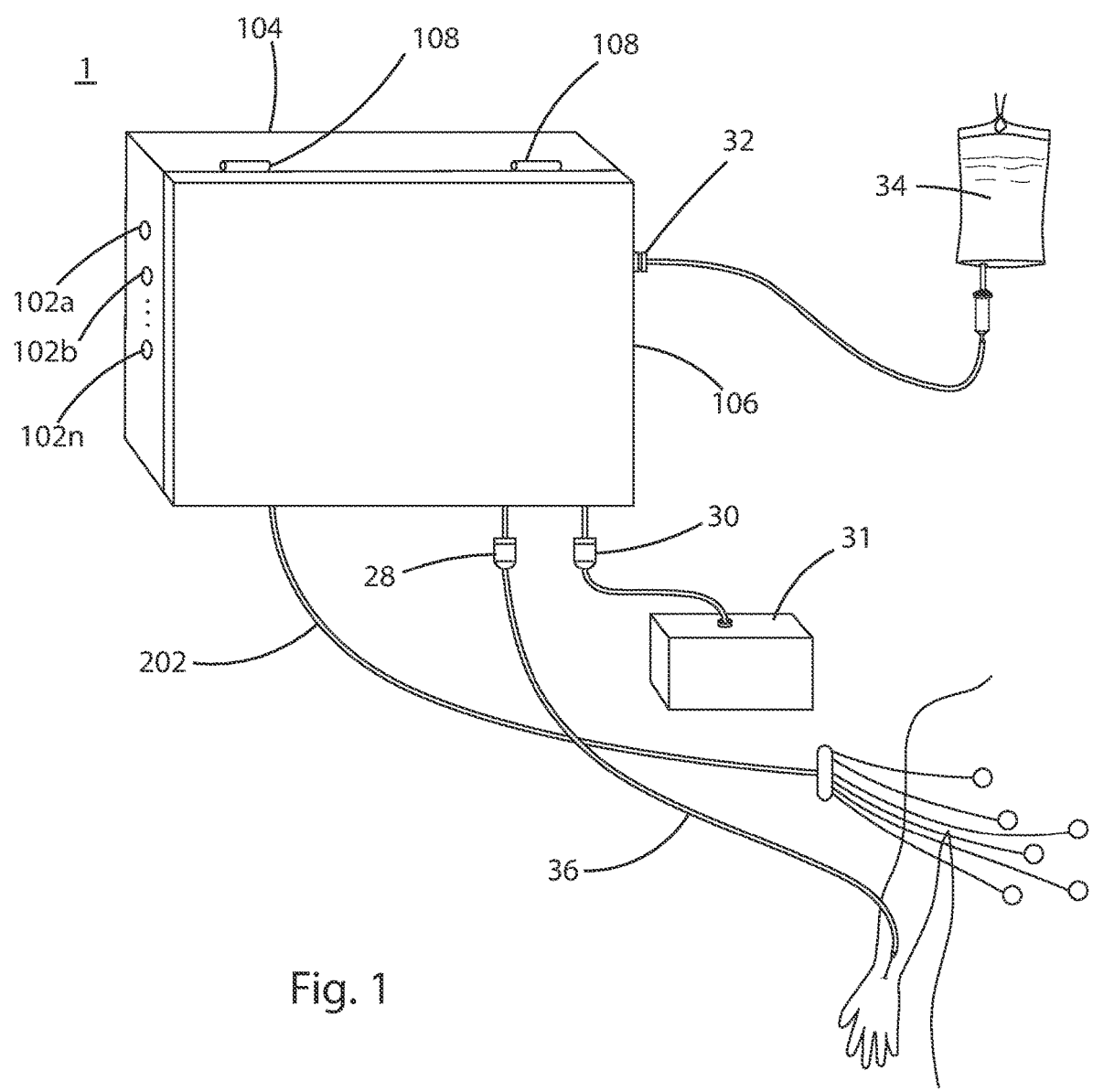
FIG. 1 is a perspective view of a device according to an embodiment of the disclosure.

FIG. 1 shows a crash box apparatus 1 according to an embodiment of the disclosure. According to one embodiment, the crash box 1 is formed from a chassis portion 104 and a cover portion 106 connected with one another by hinges 108. According to other embodiments, rather than forming crash box 1 with a hinged cover, the box has a clip-on or snap-on cover. According to yet another embodiment, the crash box is formed as a unitary structure with a slot into which a cassette including medications and fluid handling structures, as will be described below, is inserted.

According to one embodiment, crash box 1 receives signals to diagnose the condition of the patient experiencing an acute medical condition, such as cardiac arrest from, for example, a 12-lead electrocardiogram array 202. Crash box 1 delivers medications to the patient via IV/IO line 36 according to a protocol established to treat the diagnosed condition, as will be explained below. Fluid reservoir 34 provides a volume of fluid suitable for flushing medication into the patient, for example, saline or D5W, to the crash box 1 via connection 32. According to one embodiment, fluid reservoir 34 is an IV bag. According to another embodiment, reservoir 34 is housed within the crash box 1. IV/IO line 36 delivers medication and fluids to the patient via an intravenous (IV) or intraosseous (IO) needle and connects with the crash box 1 via connector 28. Waste reservoir 31 connects with crash box 1 via connector 30. Connectors 28, 30, and 32 may be Luer Lock connectors or other medically suitable connectors.

Figure 2:
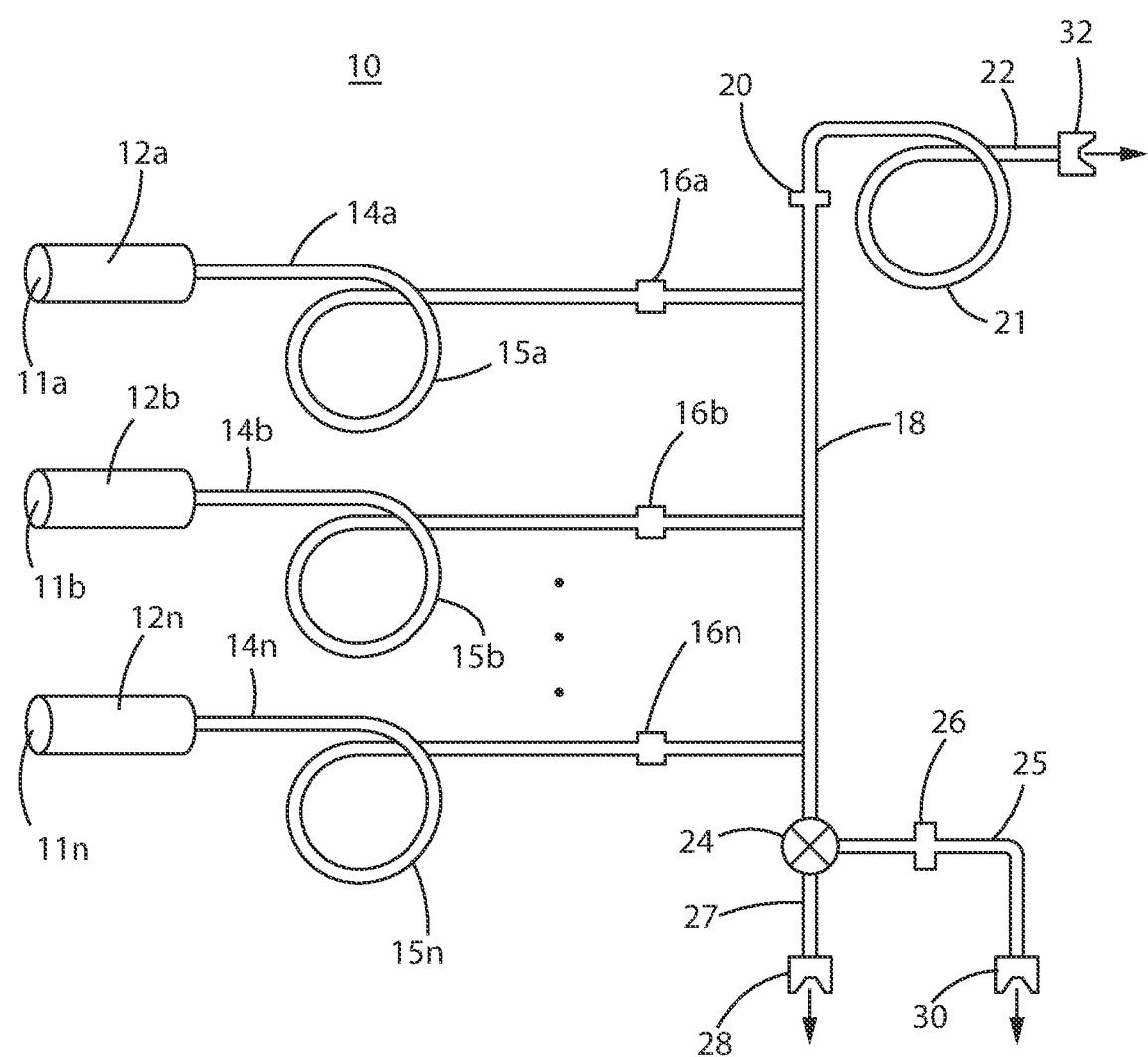
FIG. 2 is a top view of a liquid handling assembly according to an embodiment of the disclosure.
Figure 3:
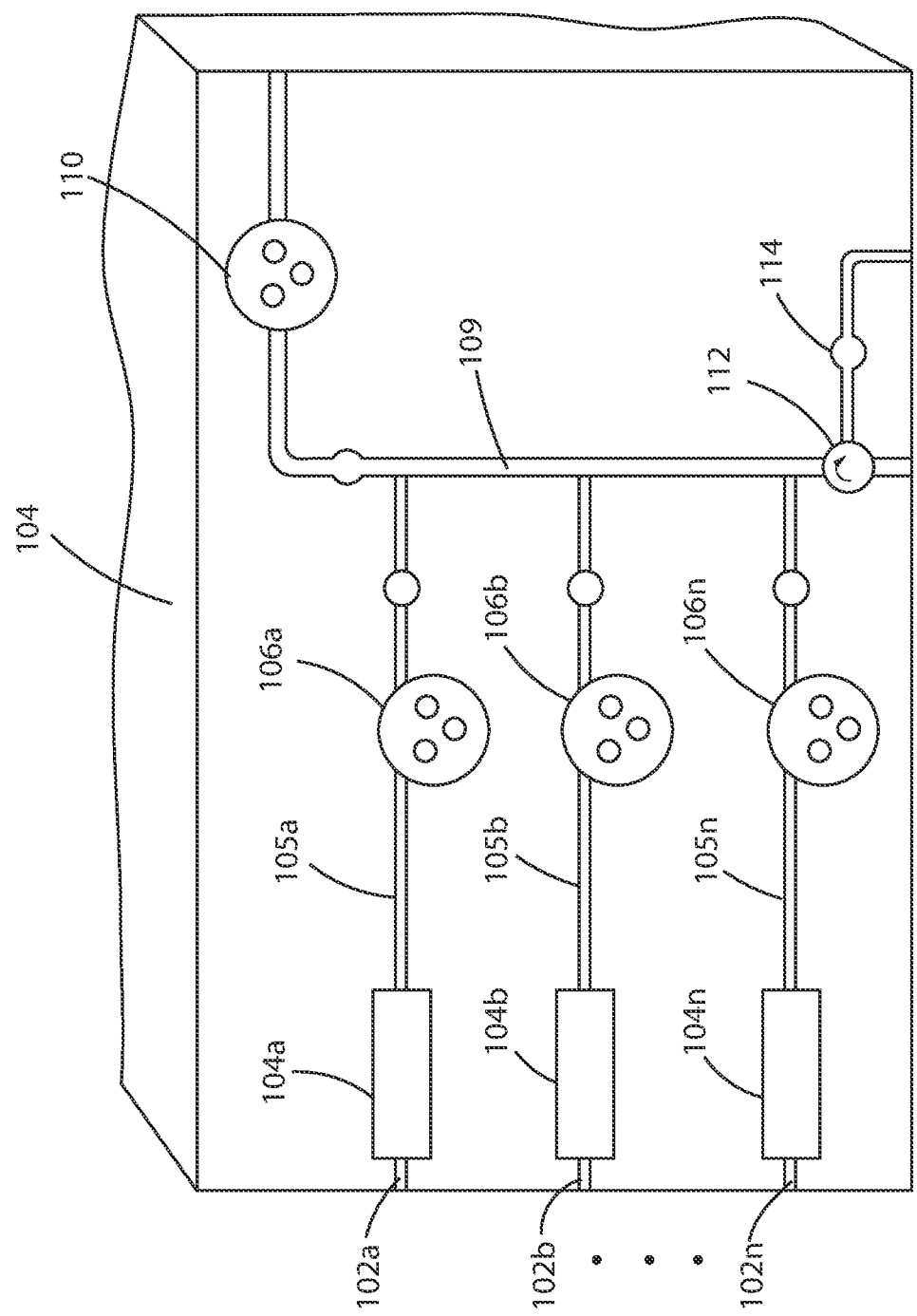
FIG. 3 is a top view of a chassis according to an embodiment of the disclosure.
Figure 4:
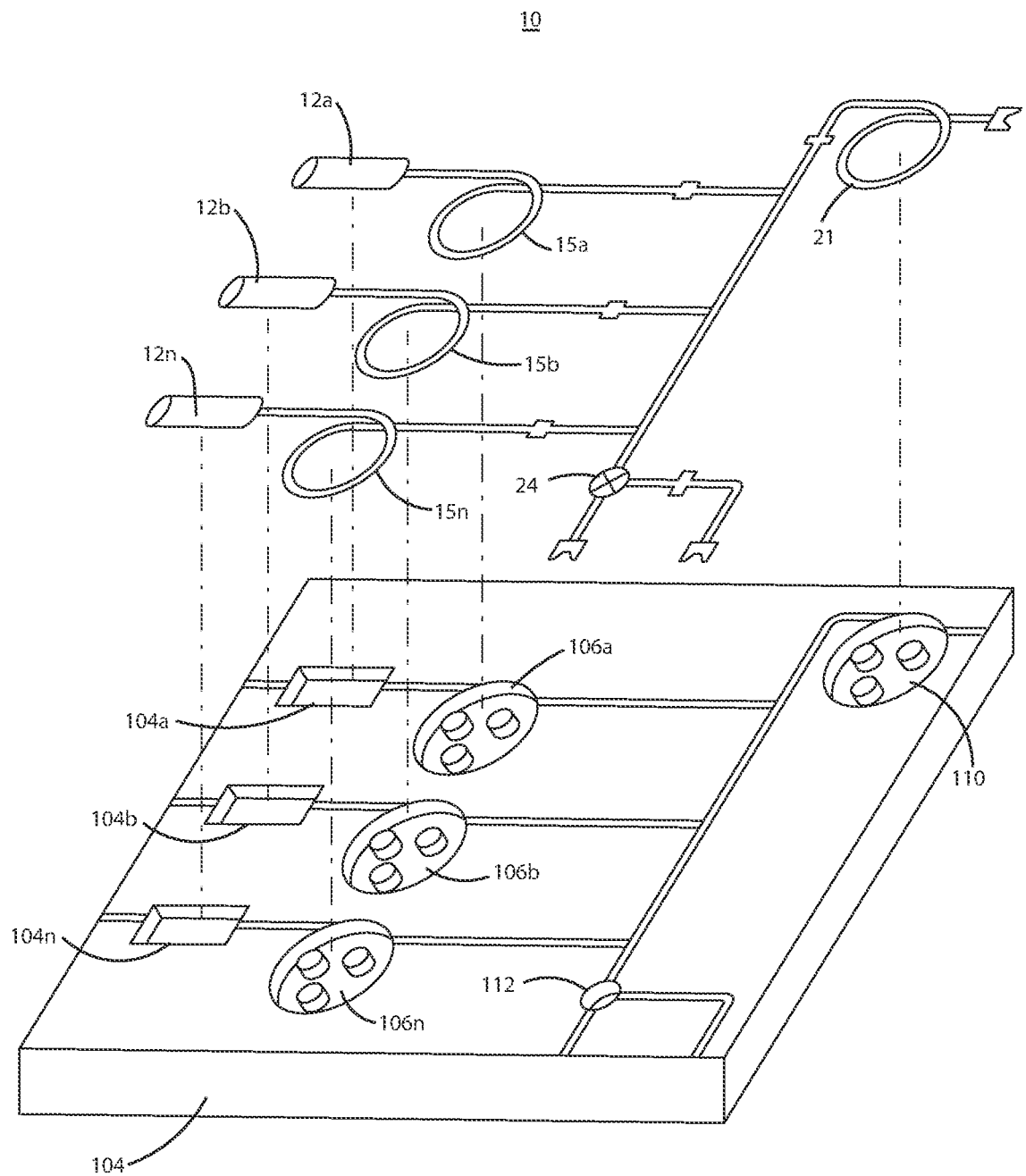
FIG. 4 is an exploded view of the assembly of FIG. 2 inserted into the chassis of FIG. 3 according to an embodiment of the disclosure.

FIG. 2 shows a liquid handling assembly 10 that is fitted into the crash box 1. FIG. 3 shows the surface of chassis 104 of crash box 1 shaped to accept insertion of the assembly 10. FIG. 4 is an exploded diagram showing the liquid handling assembly 10 fitted into the chassis 104 according to one embodiment of the disclosure.

As shown in FIG. 2, the liquid handling assembly includes a number of medication reservoirs 12a, 12b . . . 12n. The number or reservoirs corresponds to the number of different medications that may be delivered to a patient depending on the medical condition being treated. Three medication reservoirs are shown in the figure only by way of illustration and to simplify presentation, but more or fewer reservoirs could be provided within the scope of the disclosure. According to one embodiment reservoirs 12a, 12b, . . . 12n are each provided with a membrane 11a, 11b, . . . 11n that can be sealably punctured by a hypodermic needle or similar penetrating instrument to allow medications to be drawn from the reservoir and/or delivered into the reservoir manually.

Reservoirs 12a, 12b, . . . 12n may be prefilled with medications identified by protocols such as ACLS and PALS to restore heart rhythm and provide other medical treatment. These may include epinephrine, amiodarone, lidocaine, magnesium, atropine, dopamine, adenosine, diltiazem, a beta-blocker, digoxin, verapamil, aspirin, anesthetics, sedatives, or other medications. The present disclosure also includes devices to treat other acute conditions, for example, stroke, and medications to treat those conditions may be provided in one or more of the medication reservoirs. The present disclosure also includes embodiments to deliver post-arrest hypothermia to a patient to reduce the risk of damage to the central nervous system following cardiac arrest.

Conduits 14a, 14b, . . . 14n are connected with respective reservoirs 12a, 12b, . . . 12n. The conduits each include a pump loop 15a, 15b, . . . 15n. According to one embodiment, the pump loop is formed by molding or heat treating the conduit to retain the desired shape to fit into the head of a peristaltic pump, as will be described below. According to another embodiment, a frame or cassette (not shown) is provided that holds the reservoirs, conduits and other portions of the liquid handling assembly 10 in the desired configuration for insertion into the chassis 104. According to another embodiment, rather than forming pump loops 15a, 15b, . . . 15n, the lengths of the conduits is selected to provide sufficient slack to insert into a peristaltic pump head.

One-way valves 16a, 16b, ... 16n are provided on respective ones of the conduits. The valves connect the conduits to a manifold 18.

At one end of the manifold 18 is a one-way valve 20 that connects the manifold with flush line 22. Flush line 22 includes a pump loop 21 similar to the pump loops formed on conduits 14a, 14b, ... 14n. A Luer Lock or other medically suitable connector 32 is provided on the end of flush line 22 to connect with fluid reservoir 34, as shown in FIG. 1.

At the other end of manifold 18 is waste diverter valve 24. According to one embodiment, waste diverter valve 24 is a two-way stopcock with the manifold 18 connected to the input of the valve. One outlet of valve 24 is connected with waste line 25. A medically suitable connector 30 is provided at the end of waste line 25 and a one-way valve 26 is provided on waste line between the connector 30 and the valve 24. The other outlet of the waste diverter valve 24 is connected with delivery line 27. At the end of delivery line 27 is a medically suitable connector 28 to connect with IV/IO line 36, as shown in FIG. 1.

FIG. 3 shows the chassis 104 of crash box 1. Channels and cavities are formed in the surface of the chassis to correspond with the portions of the liquid handling assembly 10 shown in FIG. 2. Reservoir cavities 104a, 104b, ... 104n are provided to accommodate medication reservoirs 12a, 12b, ... 12n. At one end of cavities 104a, 104b, ... 104n are openings 102a, 102b, ... 102n extending out of the side of the chassis. As shown in FIG. 1, these openings are accessible from outside the crash box 1 to allow medical personnel to access the reservoirs such as by inserting a hypodermic needle or similar penetrating instrument through membranes 11a, 11b, ... 11n to withdraw and/or deliver medication.

Conduit vias 105a, 105b, ... 105n are shaped to accommodate conduits 14a, 14b, ... 14n, including one-way valves 16a, 16b, ... 16n. Peristaltic pump heads 106a, 106b, ... 106n are located along respective vias and are positioned to correspond with pump loops 15a, 15b, ... 15n. Manifold via 109 is provided to accommodate manifold 18 as well as one-way valve 20. Diverter valve actuator 112 is provided at a position to correspond with valve 24. The diverter valve actuator 112 is connected with a servo motor, as will be described below, that operates the valve to connect the manifold 18 with either delivery line 27 or waste line 25. Peristaltic pump head 110 is positioned to correspond with flush pump loop 21.

FIG. 4 shows an exploded view of the liquid handling assembly 10 and chassis 104. To assemble the crash box 1, a liquid handling assembly 10 is fitted into the cavities and vias of the chassis 104. Pump loops 15a, 15b, ... 15n, 21 are fitted into the corresponding peristaltic pump heads 106a, 106b, ... 106n, 110. Diverter valve 24 is fitted onto the diverter valve actuator 112. According to one embodiment, cover 106 (shown in FIG. 1) is closed over the liquid handling assembly. According to another embodiment, cover 106 includes cavities shaped to accommodate the liquid handling assembly 10 and to securely hold components of the liquid handling assembly 10 onto the chassis.

FIG. 4 shows an exploded view of the liquid handling assembly 10 and chassis 104. To assemble the crash box 1, a liquid handling assembly 10 is fitted into the cavities and vias of the chassis 104. Pump loops 15a, 15b, ... 15n, 21 are fitted into the corresponding peristaltic pump heads 106a, 106b, ... 106n, 110. Diverter valve 24 is fitted onto valve actuator 112. According to one embodiment, cover 106 (shown in FIG. 1) is closed over the liquid handling assembly. According to another embodiment, cover 106 includes cavities shaped to accommodate the liquid handling assembly 10 and to securely hold components of the liquid handling assembly 10 onto the chassis.

According to another embodiment, elements of the liquid handling assembly 10 are enclosed in a cassette housing (not shown). The cassette housing holds each of the components in a configuration to interface with the chassis. According to a further embodiment, chassis 104 is formed with a slot designed so that the cassette including the liquid handling assembly 10 is inserted into the slot. When the cassette housing is seated in the slot, components of the assembly are properly positioned with respect to the pump heads and valve actuator on the chassis 104 and held securely in place.

According to a further embodiment, one or more of reservoirs 12a, 12b, ... 12n are connected with their respective conduits 14a, 14b, ... 14n with removable connections, such as Luer Lock connectors. According to this embodiment, individual medication reservoirs can be replaced, for example, where only certain medications are used during a treatment or where one medication has exceeded its shelf-life. This embodiment helps avoid wasting the other unused or unexpired medications in the other reservoirs, potentially reducing costs.

The arrangement of the liquid handling assembly 10 and chassis 104 allows all surfaces of the crash box 1 that contact medications and other fluids that may be delivered to a patient to be removed and replaced. According to one embodiment, the crash box 1 is fitted with a liquid handling assembly 10 including medications necessary to treat a patient experiencing an acute condition, such as a cardiac arrest. The crash box 1 is stored at a convenient location, for example, on a hospital crash cart or ambulance storage bay and can be readily accessed in a code situation. Once the code is complete, the liquid handling assembly 10 is removed from the chassis and replaced with a new liquid handling assembly. This reduces the risk that infectious agents are transferred from one patient to another. In addition, because the liquid handling assembly 10 is pre-filled with medications, the crash box 1 provides medical professionals with ready access to medications that may need to be administered quickly. Alternatively, for embodiments where individual medication reservoirs can be replaced or refilled, rather than disposing of the whole liquid handling assembly 10, only individual reservoirs are replaced to ready the crash box for the next code situation.

According to another embodiment, instead of using peristaltic pumps to deliver medications into manifold 18, medication reservoirs 12a, 12b, ... 12n are comprised of pre-filled syringes connected with respective conduits 14a, 14b, ... 14n. Instead of peristaltic pump heads 106a, 106b, ... 106n, chassis 104 include syringe pump drivers. The syringe pump drivers exert force on plungers of the syringes to deliver medication from selected ones of the reservoirs into manifold 18. According to a further embodiment, fluid reservoir 34 is also replaced by a pre-filled syringe containing a sufficient volume of a medically appropriate fluid for delivering medications. This syringe is accommodated in a cavity within the chassis that is also equipped with a syringe pump driver for operating the syringe to deliver flushing fluid to manifold 18.

According to a further embodiment, instead of peristaltic pumps or syringe pumps, the system uses elastomeric pumps. An elastomeric pump (sometimes called a balloon pump) is comprised of a cavity made from an elastomeric material connected with a one-way fill valve, a flow restrictor, and an exit valve. Medication is pushed into the cavity under pressure through the one-way fill valve with the exit valve closed. Hydrostatic pressure of the medication distends the elastic walls of the cavity. The compressive force of the distended elastic walls provides pressure to drive the medication out of the cavity. When the exit valve is open, medication is forced through the flow restrictor by the hydrostatic pressure. The rate that the medication flows from the pump is determined by the elastic properties of the cavity, the dimensions of the flow restrictor, and the viscosity of the medication. The amount of medication delivered is determined based on the flow rate through the flow restrictor and the amount of time the exit valve is opened.

According to one embodiment of the disclosure, medication reservoirs 12a, 12b, . . . 12n are formed as elastomeric pumps with the elastomeric cavities filled with medications, as discussed above. The exit valves of the pumps are each computer-controlled. These computer-controlled exit valves connect the flow restrictors of the pumps with respective conduits 14a, 14b, . . . 14n. Medication is delivered to the manifold 18 via conduits 14a, 14b, . . . 14n by opening selected ones of the computer-operated valves for a period of time determined by the known flow rate of the elastomeric pump. Likewise, flushing fluid could also be delivered to manifold 18 by providing fluid reservoir 34 as an elastomeric pump and providing a computer-controlled exit valve to deliver fluid to the manifold 18.

Figure 5:
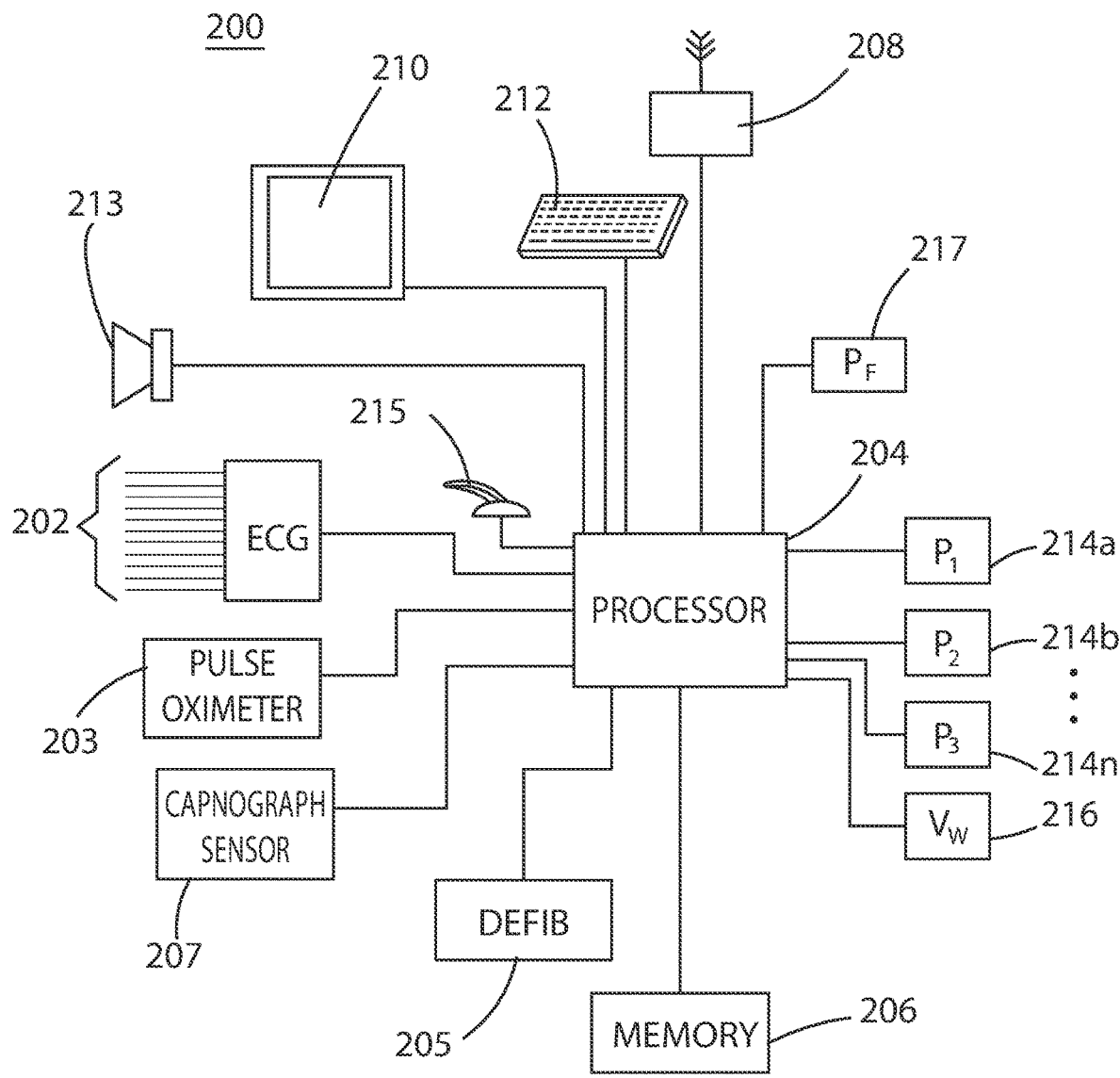
FIG. 5 is a schematic diagram of a control assembly according to an embodiment of the disclosure.

FIG. 5 shows a schematic of the electronic component system 200 provided in crash box 1. Processor 204 is connected with memory 206 to execute instructions and operate components of the crash box. Processor 204 may include components such as drivers, digital signal processing chips, programmable gate arrays, and other devices known in the field of the invention for performing calculations and operating pump motors, actuators, sensor, and the like, for transmitting and receiving instructions, and for performing the processes and operations described herein. Power is supplied to the electronic system 200 by a rechargeable battery, electrical outlet, vehicle power system, and combinations thereof (not shown).

Processor 204 receives sensor signals, such as signals from the 12-lead ECG array 202, pulse oximeter 203, capnography ($CO_2$) sensor 207, and the like that provide information about the patient's current medical condition. Processor 204 is also connected with input/output devices such as a computer keyboard 212, touchscreen 210, speaker 213, microphone 215, and wireless and/or radio frequency interface 208 (e.g., BlueTooth, WiFi, VHF, UHF). Information about the patient, including medical history, weight, age, and other information relevant to the patient's condition are received from such input/output devices. Processor 204 communicates information regarding the patient's condition, the treatment protocol, and other information to medical personnel via these input/output devices.

Processor 204 is connected with pump motors 214a, 214b, . . . 214n that drive respective pump heads 106a, 106b, . . . 106n to deliver medications from reservoirs 12a, 12b, . . . 12n to manifold 18. Likewise, the processor 204 is connected with flush pump motor 216 that drives flush pump head 110 to deliver flush liquid to the manifold 18. Processor 204 is also connected with waste diverter valve driver 217 that causes diverter valve 24 to switch the connection of the manifold 18 from the waste line 25 and delivery line 27 and vice versa. For embodiments where medication reservoirs comprise pre-filled syringes held in cavities equipped with syringe pump drivers, pump motors 214a, 214b, . . . 214n cause the pump drivers to displace the plunger of the syringes containing the selected medications to deliver a known dosage of the medication to the manifold 18. For embodiments where medications are delivered using elastomeric pumps, instead of pump motors 214a, 214b, . . . 214n, computer-operated exit valves connected with each of the elastomeric pump cavities are opened by the processor 204 for calculated periods of time to deliver the required dosage of medication to the manifold 18.

According to one embodiment, processor 204 is also connected with a defibrillation unit 205 to deliver electrical shocks to the patient as part of the treatment to restore heart function.

According to one embodiment, processor 204 includes an algorithm that determines whether the patient has an abnormal heart rhythm and whether that rhythm is one for which a protocol for treatment is known. For example, the algorithm may identify whether the patent is in: 1) Pulseless Electrical Activity (PEA) or asystole; 2) Ventricular Fibrillation or Pulseless Ventricular Tachycardia (VF/VT); 3) Bradycardia; and 4) Tachycardia. In addition, processor 204 may determine various subtypes within these abnormal rhythms, for example, wide complex tachycardia or narrow complex tachycardia.

According to one embodiment, crash box 1 may be assembled as follows. A liquid handling assembly 10 including appropriate medications is fitted into chassis 104, as shown in FIG. 4. Pump loops 15a, 15b, . . . 15n, 21 are fitted into peristaltic pump heads 106a, 106b, . . . 106n, 110. Medication reservoirs 12a, 12b, . . . 12n are fitted into cavities 104a, 104b, . . . 104n so that membranes 11a, 11b, . . . 11n are adjacent holes 102a, 102b, . . . 102n. Fluid reservoir 34 is connected with flush line 22 via connector 32. Waste line 25 is connected with waste reservoir 31 via connector 30.

Once the liquid handling assembly 10 is fitted into chassis, processor 204 executes an initiation sequence. Diverter valve 24 is set to direct flow from manifold 18 to waste line 25. Pump heads 106a, 106b, . . . 106n are activated to drive a small portion of medications through conduits 14a, 14b, . . . 14n to eliminate air bubbles from the conduit lines. Medical personnel may be prompted by processor 204 via touchscreen 210 and/or speaker 213 to confirm that air has been eliminated from conduits 14a, 14b, . . . 14n. Because one-way valves are provided between manifold 18 and conduits 14a, 14b, . . . 14n, air is prevented from flowing back into the conduits after they have been purged. Next processor 204 activates pump head 110 to pump fluid from reservoir 34 through manifold 18 and into the waste reservoir 31. This purges air from the manifold 18 and also eliminates residual medication in the manifold 18 as a result of purging conduits 14a, 14b, . . . 14n. Medical personnel are instructed to connect an IV/IO line 36 with delivery line 27 by connector 28. Processor 204 sets diverting valve 24 to connect manifold 18 with delivery line 27. Processor 204 activates pump head 110 to pump fluid from manifold 18 through IV/IO line 36 to eliminate air from the IV/IO line. Crash box 1 is now ready for use in treating a patient.

In an exemplary use scenario, crash box 1 is provided to medical personnel in a code situation, for example, in a hospital intensive care suite. A patient is found to have a life-threatening arrhythmia. An intravenous needle connected with IV/IO line 36 is inserted into the patient if IV/IO access has not already been obtained. ECG pads are applied to the patient and the ECG array 202 is connected with the pads. Other sensors including the pulse oximeter 203 and capnography sensor 207 are attached to the patient. Electrical stimulation pads are applied to the patient and connected with defibrillator 205. Processor 204 prompts medical personnel for information about the patient, for example, weight, age, and recent medication use that may be relevant to treat the arrhythmia or its underlying cause.

According to one embodiment, crash box 1 can communicate via interface 208 using a cellular telephone network, a radio frequency transceiver, or the like to send information about the patient's condition to medical personnel remote from the scene where the crash box 1 is being used to treat the patient. For example, crash box 1 may be used by emergency medical technicians to treat the patient at the scene of an accident. Information about the patient, for example, heart rhythm information, as well as information about what treatments are being given to the patient is communicated to a central office or to medical personnel at a hospital. This communication may take place using transmitting and receiving equipment located on the crash box 1 itself or the crash box may interface with other communication systems, for example, a VHF or UHF radio on board an emergency response vehicle. Likewise, personnel at the central dispatch or at the hospital can send instructions to the crash box 1, for example, to administer medications and/or deliver electrical stimulation.

Figure 6A:
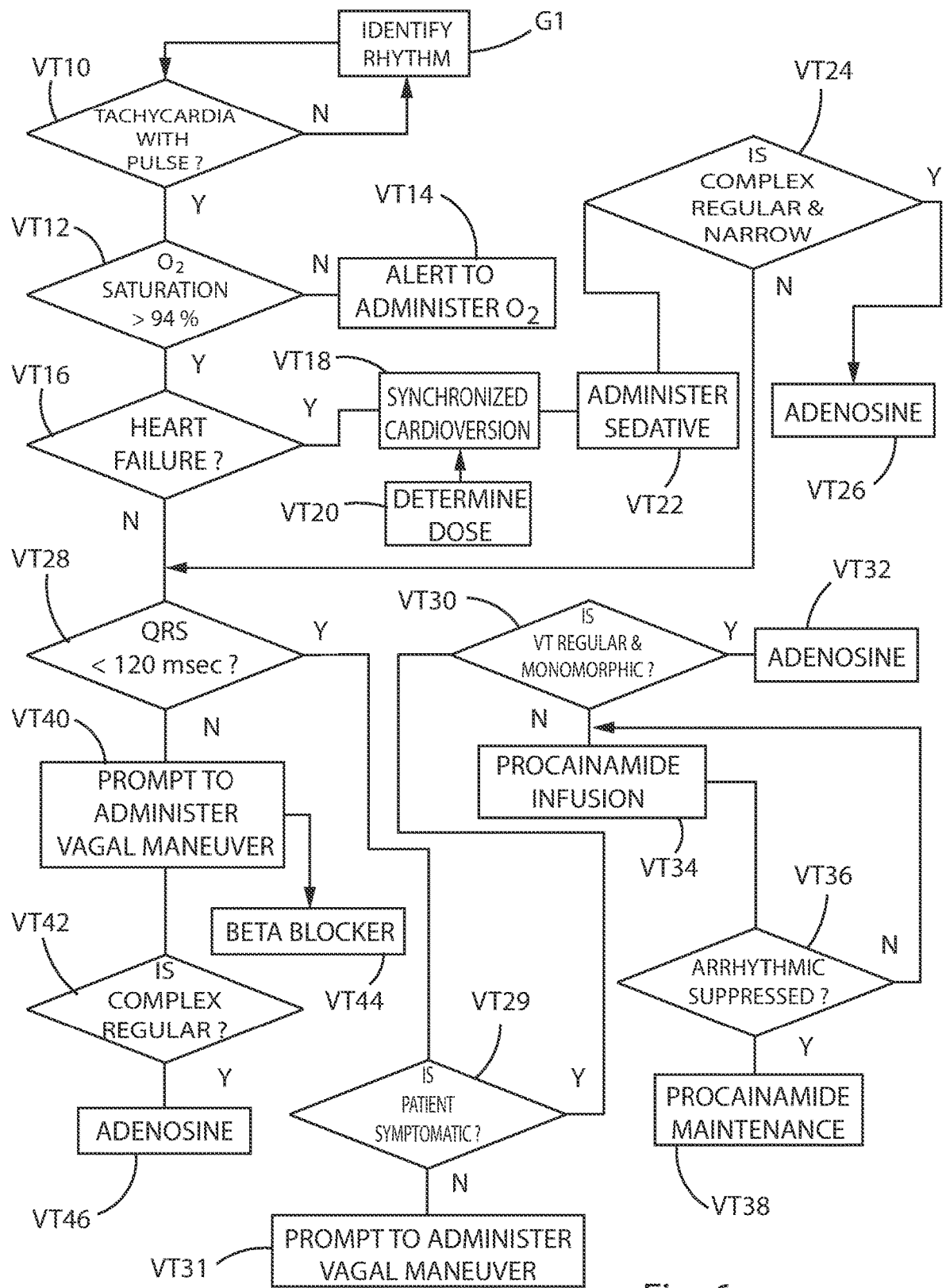
FIGS. 6a and 6b are flow charts showing an exemplary operation of a device according to an embodiment of the disclosure.
Figure 6B:
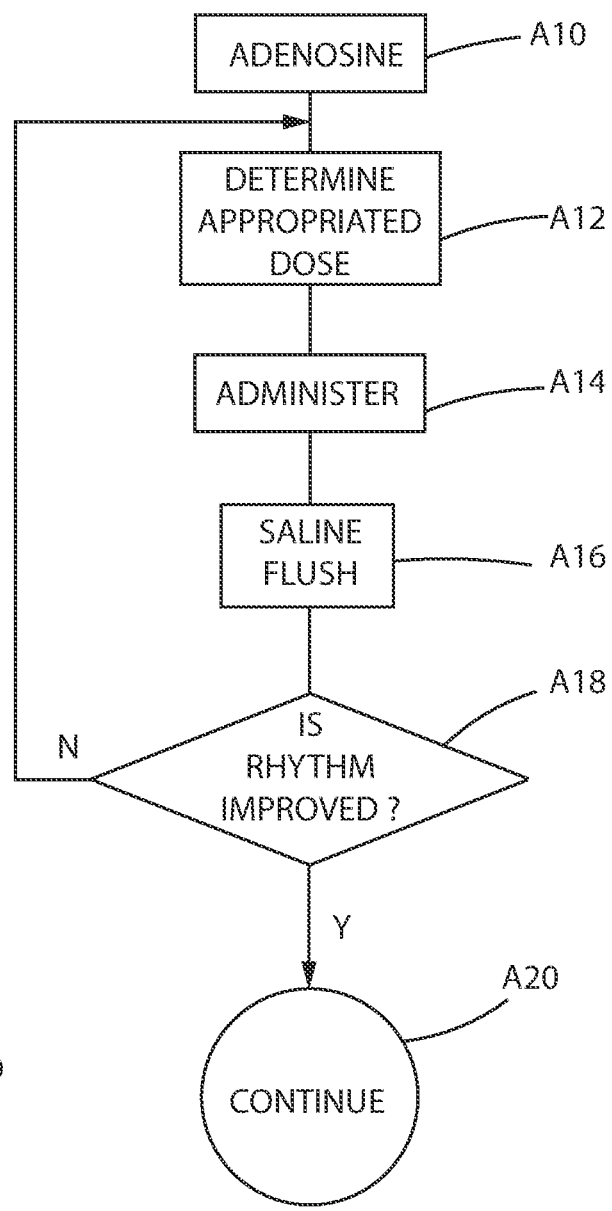

FIGS. 6a and 6b are exemplary flowcharts illustrating processing steps, algorithms, and/or computer programs for implementing an embodiment of the disclosure in the case where a patient is suffering from ventricular tachycardia (VT). Other arrhythmias, e.g., bradycardia or PEA may be diagnosed and an appropriate protocol know to those skilled in the field of the invention is executed by the crash box within the scope of the disclosure.

In this exemplary scenario, crash box 1 detects VT and implements a protocol to treat the patient starting at step VT10. At step VT 12 processor 204 determines from pulse oximeter 203 whether the patient's blood oxygen is sufficiently saturated. If 02 saturation is less than 94%, processor 204 sends a prompt via touchscreen 210 and/or via speaker 213 instructing medical personnel to administer oxygen. According to one embodiment processor 204 continues to monitor blood oxygen and provides an alert to medical personnel to increase oxygen flow to maintain sufficient blood oxygen saturation or else to diminish oxygen delivery when sufficient saturation is achieved.

At step VT 16, processor determines, based on inputs from sensors including ECG 202, pulse oximeter 203, and capnography sensor 207 and from other diagnostic information provided by medical personnel via touchscreen 210 or by voice recognition via microphone 215 whether the patient is suffering acute heart failure or has symptoms, for example, chest discomfort, altered mental state, or hypotension consistent with heart failure. If the patient is deemed to be hemodynamically unstable but has a pulse and heart failure is indicated, at step VT 18 processor begins synchronized cardioversion by applying electrical energy to the patient using defibrillator 205. Processor 204 determines the correct energy to apply for cardioversion at step VT 20 based on an analysis of the patient's ECG signals. According to one embodiment, processor 204 controls defibrillator 205 to apply cardioversion at energies specified by the ACLS. For example, where VT is narrow and regular, an initial cardioversion dose of 50 joules for an adult patient may be selected and applied synchronously with the patient's heart rhythm. According to one embodiment, crash box 1 sets defibrillator 205 according to the recommended protocol and prompts medical personnel to activate the pulse after safety precautions are taken including assuring that medical personnel and conductive surfaces are not touching the patient and that high concentrations of $O_2$ or flammable gases are not present.

At step VT 22, processor 204 administers a sedative and/or anesthetic agent to the patient. Processor activates pump head 106a to deliver a prescribed dosage, for example, 4 mg morphine into manifold 18. Processor 204 activates pump 110 to deliver flushing fluid through manifold 18 to assure complete delivery the medication to the patient. According to one embodiment, rather than administering the sedative or anesthetic agent autonomously, processor 204 prompts medical personnel whether the medication should be give using touchscreen 210 and speaker 213. If medical personnel authorize delivery of the medication, for example, by a voice command received by microphone 215, processor activates pump heads 106a and 110 as described above. According to another embodiment, to assure that no sedative or anesthetic agent remains in the manifold, processor 204 causes diverter valve to connect manifold 18 with waste line 25 and a volume of fluid is pumped through manifold 18 and into waste reservoir 31 sufficient to purge the manifold.

At step VT 24, processor 204 analyzes signals from ECG array 202 to determine if the patient's heart rhythm is regular and narrow. The crash box 1 may also prompt medical personnel to determine if the patient is asymptomatic. If the patient does not show symptoms of heart failure, the crash box may prompt medical personnel to try non-medication procedures, e.g. vagal stimulation, and to monitor the patient. If the patient is symptomatic and exhibits a regular narrow heart rhythm, crash box 1 administers adenosine according to a recommended protocol, such as ACLS.

FIG. 6b illustrates a protocol executed by crash box 1 according to an embodiment of the invention for administering adenosine. A step A12, processor 204 determines an appropriate dose. For an adult patient using the ACLS protocol, the dose is 6 mg. For a pediatric patient, processor 204 computes an appropriate dose based on the patient's weight, for example, 0.1 mg/kg. Processor activates pump head 106b connected with reservoir 12b containing adenosine at step A14 to deliver the proper dose to manifold 18. Processor 204 then activates pump head 110 at step A16 to rapidly deliver the total dose of adenosine to the patient as recommended by the ACLS or PALS, i.e., in a "rapid IV bolus." At step A18 processor 204 analyses the ECG signal to determine if the arrhythmia is improved. If there is no improvement, processor repeats steps A12, A14, A16 which may include an increased dose of adenosine of 12 mg for an adult patient. If the patient remains in symptomatic supraventricular tachycardia after the second dose of adenosine, the device will recommend expert consultation. This may include the crash box 1 providing audible instructions via speaker 213 and/or communicating information about the patient's condition to expert medical personnel at a central dispatch or hospital location via wireless interface 208. The device may also provide audible suggestions, via speaker 213, to administer other antiarrhythmic medications that may not be among those in reservoirs 12a, 12b, . . . 12n.

Returning to FIG. 6a, if at step VT16 there is no indication of heart failure, processor 204 analyses the ECG signal to determine whether the QRS complex is narrow, that is, less than 120 mSec for an adult or 90 mSec for a child. If the QRS complex is narrow, at step VT29 the processor prompts medical personnel to determine whether the patient is symptomatic. If the patient is asymptomatic, treatment without medication is indicated. At step VT 31, medical personnel are prompted to administer vagal maneuver procedures to address the arrhythmia and to monitor the patient for the return of symptoms.

If at step VT29, medical personnel determine that the patent is symptomatic, treatment using medication is indicated. At step VT30 processor 204 determines, based on the ECG signal whether the heart rhythm is regular and monomorphic. If so, adenosine is administered using the protocol described with respect to FIG. 6b. If the VT is not regular at step VT 34, the processor begins an antiarrhythmic infusion at step VT34. This infusion may include delivery of procainamide at 20-50 mg/minute. Processor 204 causes pump head 106n to deliver antiarrhythmic medication from medical reservoir 12n to the manifold 18 at the prescribed rate. Additional fluid from reservoir 34 is delivered to manifold 18 by pump head 110 to flush the medication to the patient at the prescribed rate. Processor 204 continues to monitor the ECG signal at step VT36 and continues the antiarrhythmic infusion until the arrhythmia is suppressed or until the maximum dose of the antiarrhythmic medication is reached.

At step VT28, if processor 204 determines that the QRS complex is not wide, that is, it is less than 120 mSec in an adult, at step VT40, processor prompts medical personnel to take measures to reduce rapid heartbeat using vagal stimulation, for example, carotid massage, Valsalva maneuver, and the like. If at step VT42 processor 204 determines that the patient's rhythm is regular, the crash box 1 administers adenosine at step VT 36 using the steps shown in FIG. 6b. At step VT 44, crash box 1 administers a beta blocker from one or more of the reservoirs 12n.

According to another embodiment, during the code, processor 204 stores in memory 206 data indicating the current status of the patient, including heart rhythm and other vital signs along with a record of the events of the code including the time, type and dosage of medication, the time and energy of administered electrical shocks or transcutaneous pacing, and information entered by the code team via the keyboard, touchscreen or via voice recognition. In addition, processor 204 stores a record of any communications communicated via the wireless or radio frequency interface 208, including communications regarding a patient being treated in the field and personnel at a central dispatch of hospital While illustrative embodiments of the disclosure have been described and illustrated above, it should be understood that these are exemplary of the disclosure and are not to be considered as limiting. Additions, deletions, substitutions, and other modifications can be made without departing from the spirit or scope of the disclosure. Accordingly, the disclosure is not to be considered as limited by the foregoing description.

We claim:

1. A therapeutic device comprising:
   one or more sensors, the sensors adapted to monitor parameters of an organism, the parameters relating to a medical condition;
   a plurality of medication reservoirs, each reservoir including a conduit, wherein each reservoir holds a predetermined medication;
   a manifold in fluid connection with the reservoirs via their respective conduits;
   a delivery line connected with the manifold, the delivery line adapted to deliver fluids from the manifold into the organism;
   one or more medication pumps, each medication pump adapted to deliver medication from a respective one of the reservoirs to the manifold via the conduit;
   a flush reservoir holding a flush fluid in fluid connection with the manifold;
   a flush pump in fluid connection with the flush reservoir; and
   a processor connected with the sensors, the processor including a memory storing processing instructions to interpret the parameters and to determine a recommended medication to deliver to the organism at a recommended dosage based on the parameters, the recommended medication being one of the predetermined medications, wherein the processor is operatively connected with the medication pumps and the flush pump, and wherein, on a condition that the recommended medication and the recommended dosage is determined, the processor actuates the medication pump of the reservoir holding the recommended medication to deliver the recommended dosage and actuates the flush pump to deliver a volume of the flush fluid to the manifold to deliver the medication to the organism via the manifold and the delivery line.

2. The therapeutic device of claim 1, wherein the conduits are connected with the manifold by respective one-way valves.

3. The therapeutic device of claim 1, wherein the recommended dosage comprises a rate of administration and wherein the processor actuates the one or more medication pumps and the flush pump to deliver the medication at the rate of administration.

4. The therapeutic device of claim 1, further comprising an electrical stimulation apparatus connected with the processor and with the organism, wherein signals from the processor cause the electrical stimulation apparatus to deliver electrical stimulation to the organism.

5. The therapeutic device of claim 1, further comprising:
   a waste diverting valve in fluid connection with the manifold and the delivery line;
   a diverting valve actuator in mechanical connection with the waste diverting valve and operatively connected with the processor to actuate the waste diverting valve; and
   a waste reservoir in fluid connection with the waste diverting valve, wherein on a condition that the waste diverting valve is actuated by the processor, fluid flowing from the manifold is diverted away from the delivery line and into the waste reservoir.

6. The therapeutic device of claim 1, wherein the one or more sensors includes one or more of an electrocardiogram apparatus, a pulse oximeter, and a capnography sensor.

7. The therapeutic device of claim 1, further comprising a chassis, wherein the medication pumps and the flush pump are connected with the chassis, wherein the chassis comprises a cavity, wherein the plurality of medication reservoirs and the manifold comprise a unitary assembly and wherein the cavity is shaped to accept insertion of the unitary assembly, wherein the chassis further comprises a slot adapted to receive the unitary assembly.

8. The therapeutic device of claim 1, further comprising a communication device adapted to communicate signals to and from the therapeutic device regarding the output of the one or more sensors and the actuation of the one or more medication pumps, wherein the communication signals comprise instructions to administer the predetermined medication.

9. The therapeutic device of claim 8, wherein the communication device communicates the signals to and from a location remote from the therapeutic device via radio frequency and wherein the instructions to administer the medication are received from a person remote from the organism.

10. The therapeutic device of claim 8, wherein the memory is adapted to store records of operations of the device and wherein the processor stores in the memory one or more of an output of the one or more sensors, a record of the actuation of the one or more medication pumps, and the communication signals.

11. A therapeutic device comprising:
a cassette assembly;
a chassis, the chassis defining a slot configured to receive the cassette assembly;
the cassette assembly including:
  a housing defining an internal volume,
  a plurality of reservoirs positioned within the internal volume, one of the plurality of reservoirs being a flush reservoir, the flush reservoir containing a flush fluid,
  a manifold in fluid connection with each of the reservoirs on a condition that the cassette assembly is operably coupled to the chassis, the flush reservoir being fluidly coupled to the manifold upstream of a coupling location for each of the other reservoirs of the plurality of reservoirs, and
  a delivery line fluidically coupled to the manifold, the delivery line adapted to deliver a fluid; and
the chassis including:
  a drive assembly positioned to deliver the fluid from at least one of the plurality of reservoirs to the manifold, and
  an electronic component system including a processor operably coupled to a memory storing processing instructions to interpret a plurality of parameters and control delivery of the fluid.

12. The therapeutic device of claim 11, wherein the plurality of parameters are associated with a medical intervention in response to an acute medical condition.

13. The therapeutic device of claim 11, wherein:
each reservoir of the plurality of reservoirs is a pre-filled syringe;
the pre-filled syringes include a plurality of medication syringes; and
each of the medication syringes contains a different medication.

14. The therapeutic device of claim 13, wherein each pre-filled syringe is independently actuatable.

15. The therapeutic device of claim 13, wherein:
each pre-filled syringe includes a plunger;
the drive assembly includes a plurality of syringe pump drivers; and
each plunger is positioned to receive a force from one of the syringe pump drivers.

16. The therapeutic device of claim 11, wherein the delivery line is fluidically coupled to a patient via patient via one of an intravenous or intraosseous needle.

17. The therapeutic device of claim 11, wherein an external fluid reservoir is fluidically coupled to the delivery line.

18. The therapeutic device of claim 11, wherein the instructions include:
determining a recommended medication to deliver;
determining a recommended dosage based on the parameters;
actuating a first portion of the drive assembly operatively coupled to one reservoir of the plurality of reservoirs containing a medication to deliver the recommended dosage to the manifold; and
following the delivery of the recommended dosage to the manifold, actuating a second portion of the drive assembly operatively coupled to the flush reservoir to deliver a volume of the of the flush fluid to the manifold.

19. The therapeutic device of claim 11, wherein the electronic component system includes a communication device configured to communicate signals regarding actuation of the drive assembly.

20. The therapeutic device of claim 11, further comprising:
at least one sensor configured to monitor at least one parameter of the plurality of parameters, the sensor includes one or more of an electrocardiogram apparatus, a pulse oximeter, and a capnography sensor.

* * * * *